United States Patent [19]
Abe et al.

[11] Patent Number: 5,425,787
[45] Date of Patent: Jun. 20, 1995

[54] METHOD FOR CRYSTALLIZATION OF α-L-ASPARTYL-L-PHENYLALANINE METHYL ESTER

[75] Inventors: Sou Abe; Shinichi Kishimoto, both of Kawasaki, Japan

[73] Assignee: Ajinomoto Co., Inc., Tokyo, Japan

[21] Appl. No.: 203,472

[22] Filed: Feb. 28, 1994

Related U.S. Application Data

[63] Continuation of Ser. No. 967,234, Oct. 27, 1992, abandoned.

[30] Foreign Application Priority Data

Oct. 30, 1991 [JP] Japan .................................. 3-284590
Apr. 22, 1992 [JP] Japan .................................. 4-102918

[51] Int. Cl.$^6$ .................................. C07C 229/00
[52] U.S. Cl. .................................. 23/295 R; 530/801; 560/40; 560/41
[58] Field of Search .................. 23/295 R; 560/41; 530/801, 342; 203/7

[56] References Cited

U.S. PATENT DOCUMENTS

| | | | |
|---|---|---|---|
| 3,901,871 | 8/1975 | Anderson | 260/112.5 |
| 4,994,605 | 2/1991 | Kishimoto et al. | 562/445 |
| 5,248,806 | 9/1993 | Kishimoto et al. | 560/41 |
| 5,266,719 | 11/1993 | Kishimoto et al. | 500/41 |
| 5,292,923 | 3/1994 | Kato et al. | 560/40 |
| 5,298,648 | 3/1994 | Ebisawa et al. | 560/41 |
| 5,304,671 | 4/1994 | Abe et al. | 560/41 |

FOREIGN PATENT DOCUMENTS

| | | | |
|---|---|---|---|
| 0091787 | 10/1983 | European Pat. Off. | |
| 0128694 | 12/1984 | European Pat. Off. | 560/41 |
| 0227301 | 7/1987 | European Pat. Off. | 560/41 |
| 0256517 | 2/1988 | European Pat. Off. | 560/41 |
| 0362706 | 4/1990 | European Pat. Off. | |
| 0405273 | 1/1991 | European Pat. Off. | |

OTHER PUBLICATIONS

"Chemical Engineer's Handbook" by Perry et al; 5th ed.; McGraw-Hill N.Y.; 1973; pp. 10–38.

*Primary Examiner*—Gary P. Straub
*Assistant Examiner*—Timothy C. Vanoy
*Attorney, Agent, or Firm*—Oblon, Spivak, McClelland, Maier, & Neustadt

[57] ABSTRACT

The problems in crystallization of α-L-aspartyl-L-phenylalanine methyl ester, namely, problems in crystal slurry properties in solid-liquid separation, scaling at heat transfer surfaces, and the like, are solved by a method for crystallization of α-L-aspartyl-L-phenylalanine methyl ester which comprises cooling a solution of α-L-aspartyl-L-phenylalanine methyl ester by indirect heat exchange with a coolant while stirring, wherein the solution is cooled by circulating a coolant while continuously adding an aqueous solution of α-L-aspartyl-L-phenylalanine methyl ester dropwise to a crystallizing solution of α-L-aspartyl-L-phenylalanine methyl ester having a temperature difference of not greater than 20° C. from the coolant, thereby to keep a temperature difference of not greater than 20° C. between the coolant and the crystallizing solution.

6 Claims, 2 Drawing Sheets

METHOD FOR CRYSTALLIZATION OF α-L-ASPARTYL-L-PHENYLALANINE METHYL ESTER

This application is a Continuation of application Ser. No. 07/967,234, filed on Oct. 27, 1992, now abandoned.

BACKGROUND OF THE INVENTION

1. Field of the Invention

The present invention relates to a method for the preparation of α-L-aspartyl-L-phenylalanine methyl ester (hereafter abbreviated as α-APM). α-APM is a peptide sweetener which exhibits a sweetness about 200 times that of sucrose.

2. Discussion of the Background

α-APM has been widely used as a dieting sweetener in recent years because of its high quality sweetness and low calorie content. It is thus expected that its demand over the world will exceed 10,000 tons through 1995.

The following examples of methods for preparing α-APM on an industrial scale are known:

(1) A method for preparing α-APM which comprises binding an N-substituted aspartic anhydride to L-phenylalanine methyl ester in an organic solvent, splitting the substituent off in a conventional manner (U.S. Pat. No. 3,786,039), contacting the formed α-APM including impurities with a hydrohalogenic acid to obtain α-APM hydrohalide and then neutralizing the hydrohalide;

(2) A method which comprises converting α-L-aspartyl-L-phenylalanine in a solvent mixture of water, methanol and hydrochloric acid into the corresponding methyl ester to form α-APM hydrochloride, and neutralizing the hydrochloride to give α-APM (Japanese Patent Application Laid-Open No. 53-82752); and (3) A method which comprises condensing an N-substituted aspartic acid with phenylalanine methyl ester in the presence of enzyme and then removing the substituent (Japanese Patent Application Laid-Open No. 55-135595).

In the methods (1) through (3) described above, α-APM is eventually crystallized using a solvent which dissolves α-APM, such as water at a high temperature or a hydrated lower alcohol. The crystals are isolated and dehydrated using an apparatus for solid-liquid separation, such as a centrifugal machine, and then dried to obtain the final product.

Crystallization methods include cooling crystallization, neutralization crystallization and concentration crystallization. However, α-APM decomposes to diketopiperazine (and other compounds) at high temperatures, such as those often employed in concentration crystallization. As a result, cooling crystallization is preferred when considering the temperature stability of α-APM.

Cooling crystallization is generally carried out using a stirring crystallizer having a heat transfer surface for cooling, or a crystallizer equipped with a heat exchanger in an external circulation system. When cooling crystallization is performed using a crystallizer accompanied by forced fluidization, such as stirring or external circulation, fine needles of α-APM are usually obtained. Such fine needles have poor properties for solid-liquid separation, such as a poor filterability or dewaterability. As a result, conventional methods (for example, a method for crystallization which comprises cooling a hot aqueous solution of APM by indirect heat transfer with a coolant at a low temperature) requires a large filtering area for solid-liquid separation.

In addition, such methods result in crystals precipitating in large amounts upon crystallization. The precipitated crystals adhere to the cooling surface, thus markedly reducing the cooling efficiency.

In order to efficiently cool a crystallizing solution, scales (adhered crystals) must be removed from cooling surface. Continuous crystallization generally provides high productivity on an industrial scale, however, if scaling occurs, it is necessary to stop operation often. Then productivity is unavoidably reduced. Although scaling does not cause a serious problem in an experiment for a short period of time using a glass vessel, such as those frequently used in a research laboratory, scaling often creates a serious problem over longer periods of time using a metallic apparatus, such as those used for continuous crystallization on an industrial scale.

SUMMARY OF THE INVENTION

Accordingly, one object of the present invention is to provide a novel method for the preparation of α-L-aspartyl-L-phenylalanine methyl ester, which reduces the amount of scale deposited on heat transfer surfaces of a crystallizer.

A further object of the present invention is to provide a novel method for the crystallization of α-APM which improves the solid-liquid separation properties of a crystal slurry of α-APM.

A further object of the present invention is to provide a marked improvement of methods for crystallization of α-APM from a solution of α-APM.

These and other objects which will become apparent during the following discussion of the preferred embodiments have been provided by a method for the crystallization of α-APM, comprising cooling and stirring a crystallizing solution of α-APM, wherein the cooling is conducted by indirect heat exchange with a coolant, and the crystallizing solution of α-APM having a temperature not greater than 20° C. higher than the temperature of the coolant; and circulating the coolant while continuously feeding an aqueous solution of α-APM to the crystallizing solution of α-APM.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE PREFERRED EMBODIMENTS

The problems described above can be overcome in continuous crystallization by maintaining the temperature difference between the crystallization solution and the coolant to 20° C. or less. Where the temperature difference is more than 20° C., scaling occurs to a remarkable extent, and the temperature of the crystallizing solution subsequently increases. Accordingly, the operation must be discontinued many times to remove scales. Where the temperature difference is 10° C. or below, scaling is minimized. Therefore, maintaining the temperature difference between the crystallization solution and the coolant to 10° C. or less is extremely preferred in operation.

On the other hand, the aqueous solution of α-APM fed into the crystallizing solution (the "feed" solution) should have as high a concentration as possible, to maximize the productivity (efficiency for a given volume in an apparatus) and to obtain crystals having excellent solid-liquid separation properties. As described above, however, α-APM is converted into diketopiperazine at a high temperature. Diketopiperazine is harmless (no toxicity), but exhibits no sweetness. Therefore, it is preferred that the temperature of the feed solution be generally in the range of 30° to 80° C. and the solution concentration be about a saturation concentration.

The solvent is not limited to water, but the use of solvent mixture of a lower alcohol (e.g., a $C_1$–$C_4$ alcohol) and water is advantageous since the solubility of α-APM increases at high temperatures (for example, above 40° C.).

The present invention is effective in a semi-batch system, but exhibits improved effects in continuous operation. Thus, preferably, cooling and stirring the crystallizing solution are conducted simultaneously. Also preferred is cooling by indirect means; that is, heat transfer between the coolant medium and the crystallizing solution occurs through a partition, such as the wall of a crystallizer, a coil in the crystallizing solution through which coolant passes, a jacket surrounding part or all of the crystallizing solution or the crystallizer which conducts the coolant medium, etc. In the present method, particularly preferred indirect cooling means include equipping a crystallizer with a jacket, a cooling plate, a coil or an external heat exchanger.

Figure 2B:
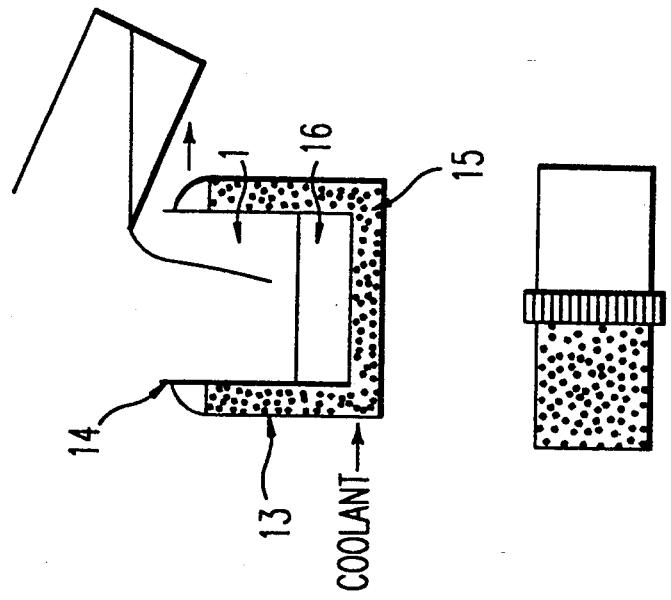
FIG. 2 shows the difference between direct (FIG. 2(A)) and indirect (FIG. 2(B)) cooling means.
Figure 2A:
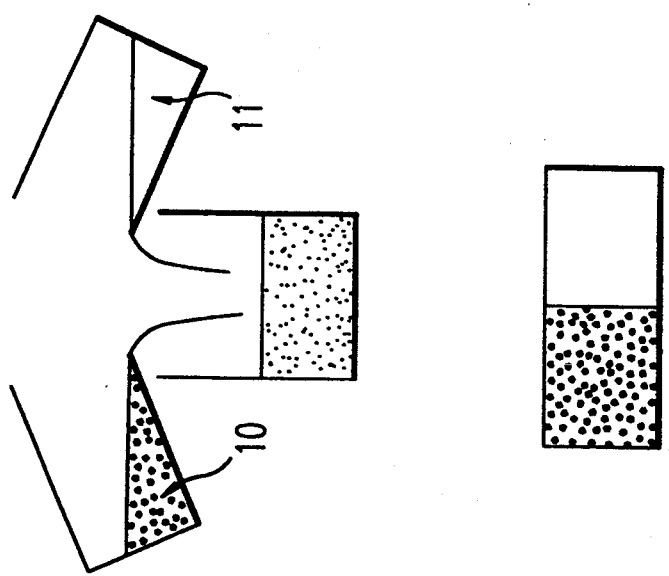

As shown in FIG. 2, indirect cooling means differ from direct cooling means. FIG. 2(A) shows an example of direct cooling, in which heat transfer between the coolant medium 10 and the crystallizing solution 11 occurs directly, by mixing the cooling medium directly with the crystallizing solution. On the other hand, FIG. 2(B) shows an example of indirect cooling, using a container 12 equipped with a jacket 13. The partition 14 between container 12 and jacket 13 conducts heat between the coolant medium 15 and the crystallizing solution 16 in the apparatus of FIG. 2(B).

It is also preferred that the crystallization be conducted in a crystallizing apparatus having metal surfaces. Thus, the crystallizing solution of α-APM is contained in an apparatus having at least one metal heat exchange surface. A particularly preferred metal for the crystallizing apparatus is stainless steel.

The properties of the crystal slurry for solid-liquid separation are excellent. The cooling efficiency of crystallizer is good, because scaling occurs at a cooling surface only with difficulty. Continuous operation can be performed over a long period of time.

Other features of the present invention will be come apparent in the course of the following descriptions of exemplary embodiments which are given for illustration of the invention, and are not intended to be limiting thereof.

EXAMPLE 1

Figure 1:
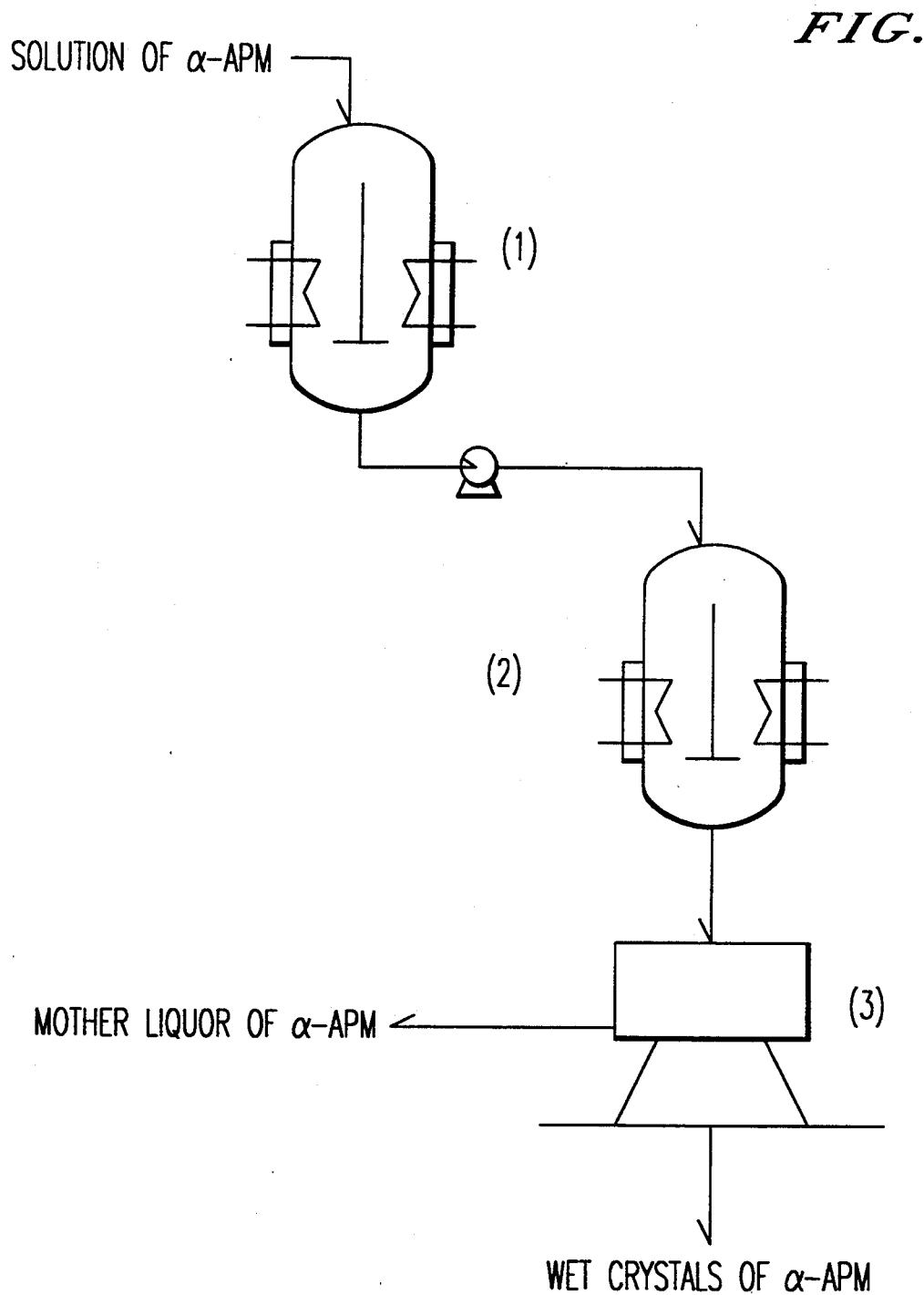
FIG. 1 sketches the method and apparatus used in Example 1.

As shown in FIG. 1, an α-APM slurry was charged in a stainless steel crystallizer 1 (for industrial use) having a volume of 4 m³, equipped with a cooling coil and stirrer A coolant having a temperature of 0° C. was circulated in the cooling coil, thus setting the temperature of the slurry at 5° C. A 3.5% by weight aqueous solution of α-APM having a temperature of 60° C. was continuously fed into the crystallizer containing the cold slurry at a rate of 0.5 m³/hr. The slurry was withdrawn from the crystallizer and transferred to slurry holding tank 2 at the same rate (0.5 m³/hr), to keep a constant volume of slurry in the crystallizer. The initial slurry was gradually replaced by crystallizing slurry. The stirrer was set at 30 rpm. Crystallization was carried out for four consecutive days, during which tile temperature of slurry was kept at 4° to 6° C.

The slurry in slurry holding tunk 2 was immediately charged to centrifuge 3 having an inner diameter of 48 inches for solid-liquid separation (the corresponding centrifugal effect is 600 G). The water content in the every resulting wet crystals of α-APM was in the range of 39–41%. After completion of the crystallization, the slurry remaining in crystallizer 1 was withdrawn, and the cooling surface was examined. No serious scaling was noted.

EXAMPLE 2

The same procedures as in Example 1 were carried out, except that the temperature of the slurry was kept at 15° C. or below (a maximum temperature difference of 15° C. between coolant and slurry), and the continuous crystallizing operation was performed for 3 days. The water content in tile every thus-obtained wet crystals of α-APM was in the range of 38–46%. Slight scaling was noted.

Comparative Example 1

The same procedures as in Example 1 were carried out, except that the temperature of the slurry was set at 25° C. Scaling occurred to a remarkable extent, and the cooling efficiency was reduced to such an extent that the temperature of 25° C. could not be maintained. In addition, the slurry temperature gradually increased to finally reach 30° C. on the second day. Thereafter, the solution temperature showed a tendency to still increase, and the total heat transfer coefficient at the cooling surface clearly decreased. The situation indicated that no crystal recovery is expected, and the crystallization operation was discontinued. The water content of the final obtained wet crystals of α-APM was 52%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for crystallization of α-L-aspartyl-L-phenylalanine methyl ester, comprising forming a cold saturated solution of α-APM, which is formed by indirect heat exchange with a coolant, and the said solution of α-APM having a temperature not greater than 20° C. higher than the temperature of the coolant; and stirring said solution while continuously feeding an aqueous feed solution of α-APM to the cold saturated solution of α-APM.

2. The method of claim 1, wherein said temperature difference between said coolant and said cold saturated solution of α-L-aspartyl-L-phenylalanine methyl ester is not greater than 10° C.

3. The method of claim 1, wherein said forming and stirring are conducted simultaneously.

4. The method of claim 1, wherein said cold saturated solution of α-APM is contained in an apparatus having a metal heat exchange surface.

5. The method of claim 4, wherein said metal is stainless steel.

6. The method of claim 1, further comprising the step of withdrawing an amount of said cold saturated solution corresponding to the amount of said aqueous solution of α-APM fed into said cold saturated solution.

* * * * *